United States Patent
Yoon et al.

(10) Patent No.: US 11,913,064 B2
(45) Date of Patent: Feb. 27, 2024

(54) MOLECULAR BEACON-BASED OPTICAL GENE BIOSENSOR EMPLOYING RETRO-REFLECTION AND QUANTITATIVE ANALYSIS METHOD OF NUCLEIC ACID MOLECULE

(71) Applicant: AJOU UNIVERSITY INDUSTRY-ACADEMIC COOPERATION FOUNDATION, Suwon-si (KR)

(72) Inventors: Hyun-Chul Yoon, Seoul (KR); Jae-Ho Kim, Suwon-si (KR); Yong-Duk Han, Seongnam-si (KR); Hyeong-Jin Chun, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 717 days.

(21) Appl. No.: 16/498,877

(22) PCT Filed: Mar. 9, 2018

(86) PCT No.: PCT/KR2018/002812
§ 371 (c)(1),
(2) Date: Sep. 27, 2019

(87) PCT Pub. No.: WO2018/199465
PCT Pub. Date: Nov. 1, 2018

(65) Prior Publication Data
US 2021/0189471 A1 Jun. 24, 2021

(30) Foreign Application Priority Data

Apr. 26, 2017 (KR) .......................... 10-2017-0053397

(51) Int. Cl.
*G01N 21/55* (2014.01)
*G02B 5/126* (2006.01)
(Continued)

(52) U.S. Cl.
CPC ........... *C12Q 1/6825* (2013.01); *G01N 21/55* (2013.01); *G02B 5/126* (2013.01); *G02B 5/128* (2013.01);
(Continued)

(58) Field of Classification Search
CPC .. C12Q 1/6825; C12Q 1/6816; C12Q 1/6818; C12Q 2545/114; C12Q 2563/149;
(Continued)

(56) References Cited

U.S. PATENT DOCUMENTS 4,626,501 A * 12/1986 Landes ................. C07H 21/00
536/25.4
2005/0069895 A1* 3/2005 Woudenberg ........ G01N 33/532
435/6.12
(Continued)

OTHER PUBLICATIONS

Tan et al., "Molecular Beacons : A Novel DNA Probe for Nucleic Acid and Protein Studies", Chem. Eur. J. 2000, 6, 7 (Year: 2000).*
(Continued)

*Primary Examiner* — Samuel P Siefke
*Assistant Examiner* — Henry H Nguyen
(74) *Attorney, Agent, or Firm* — Sughrue Mion, PLLC

(57) ABSTRACT

An optical gene biosensor is disclosed. The optical gene biosensor includes a substrate; a molecular beacon anchored to the substrate, wherein the molecular beacon includes an oligonucleotide specifically binding to a target nucleic acid molecule and a first compound bound to a first terminal of the oligonucleotide; an optical marker specifically binding to the first compound, wherein the optical marker is configured to retro-reflect irradiated light; a light source for irradiating
(Continued)

the optical marker with light; and a light-receiver for receiving light retro-reflected from the optical marker. The optical gene biosensor may perform accurate quantitative analysis of a target nucleic acid molecule using both non-spectral and spectral light sources.

17 Claims, 6 Drawing Sheets

Specification includes a Sequence Listing.

(51) Int. Cl.
    *G02B 5/128*     (2006.01)
    *G02B 5/12*     (2006.01)
    *C12Q 1/6825*     (2018.01)

(52) U.S. Cl.
    CPC ........... *G01N 2021/551* (2013.01); *G01N 2201/0636* (2013.01); *G02B 5/12* (2013.01)

(58) Field of Classification Search
    CPC ....... C12Q 2565/101; C12Q 2565/619; G01N 21/55; G01N 2021/551; G01N 2201/0636; G01N 21/1717; G01N 2021/1742; G02B 5/126; G02B 5/128; G02B 5/12; B82Y 5/00
    See application file for complete search history.

(56) References Cited

U.S. PATENT DOCUMENTS

| | | | |
|---|---|---|---|
| 2006/0084101 A1* | 4/2006 | Xu | G01N 33/581<br>435/7.5 |
| 2009/0034902 A1* | 2/2009 | Izmailov | B82Y 15/00<br>385/12 |
| 2009/0104614 A1* | 4/2009 | Tsourkas | C12Q 1/6818<br>536/24.31 |
| 2009/0137418 A1* | 5/2009 | Miller | B82Y 30/00<br>506/17 |
| 2010/0028453 A1* | 2/2010 | Yoo | C08J 3/12<br>424/178.1 |
| 2015/0361483 A1* | 12/2015 | Lo | C12Q 1/6806<br>536/23.1 |

OTHER PUBLICATIONS

Xian Fang et al., "Molecular beacon Based biosensor for the Sequence-specific detection of DNA Using DNA-capped gold nanoparticles-streptavidin conjugates for signal amplification", Microchim Acta, Jul. 23, 2013 (Electronic publishing), pp. 1271-1277, vol. 180, Nos. 13-14.

Yong Duk Han et al, "Retroreflective Janus Microparticle as a Nonspectroscopic Optical Immunosensing Probe", Applied Materials & Interfaces, Apr. 15, 2016, pp. 10767-10774, vol. 8, No. 17.

Catherine Situma et al., "Immobilized Molecular Beacons: A New Strategy Using UV-activated Poly(methyl methacrylate) Surfaces to Provide Large Fluorescence Sensitivities for Reporting on Molecular Association Events", Analytical Biochemistry, Dec. 20, 2006 (Electronic publishing), pp. 35-45, vol. 363, No. 1.

Balakrishnan Raja et al., "An Embedded Microretroreflector-based Microfluidic immunoassay Platform", Lab on a Chip, 2016, pp. 1625-1635, vol. 16, No. 9.

Gavin Garvey et al., "Mcroretroreflector-Sedimentation Immunoassays for Pathogen Detection", Analytical Chemistry, Aug. 18, 2014, pp. 9029-9035, vol. 86, No. 18.

International Search Report PCT/KR2018/002812, dated Jun. 7, 2018.

* cited by examiner

[FIG. 1]
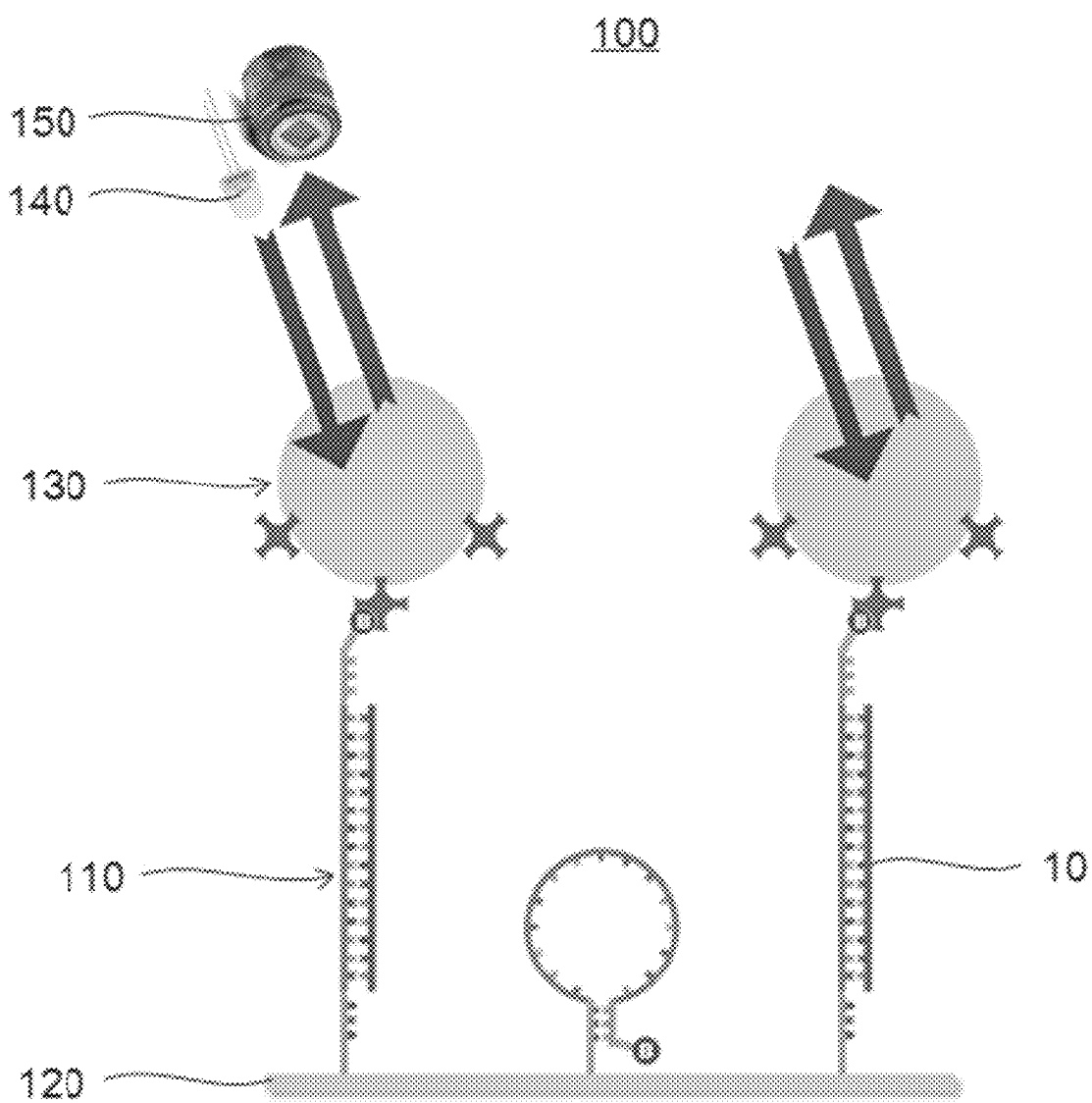

[FIG. 2]
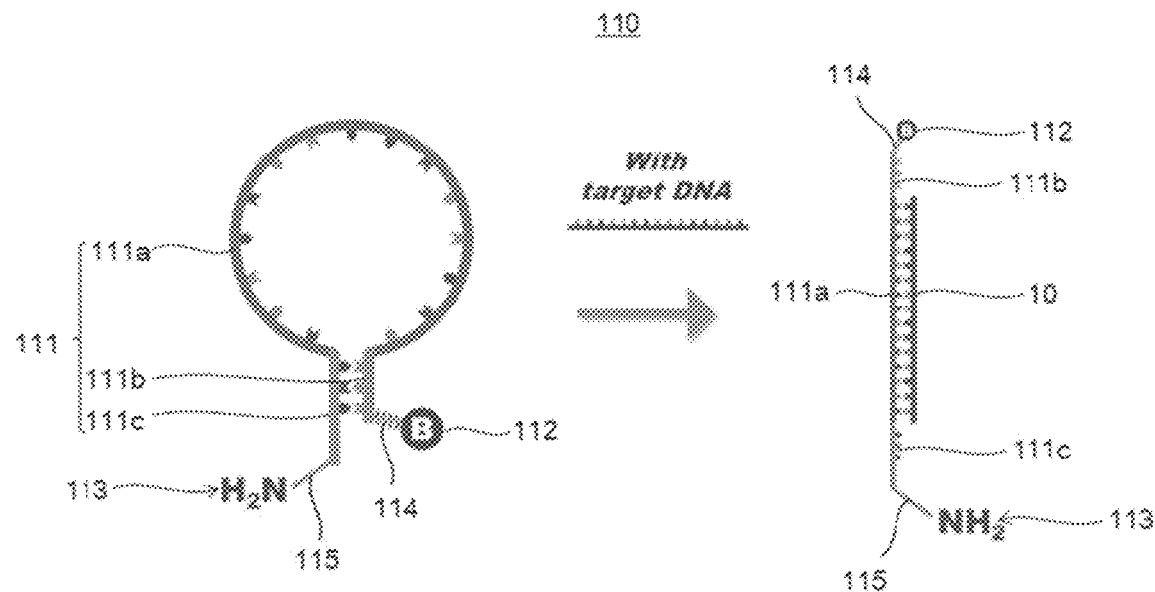
[FIG. 3A]
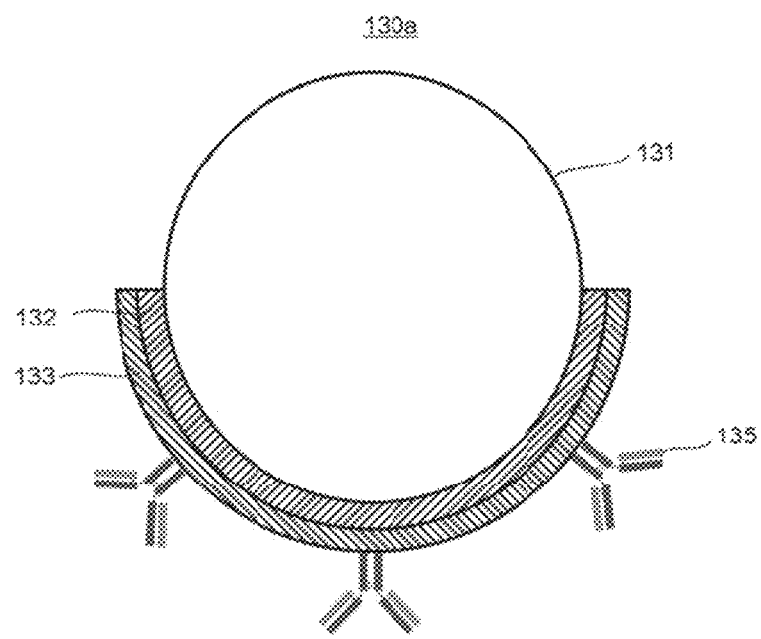

[FIG. 3B]
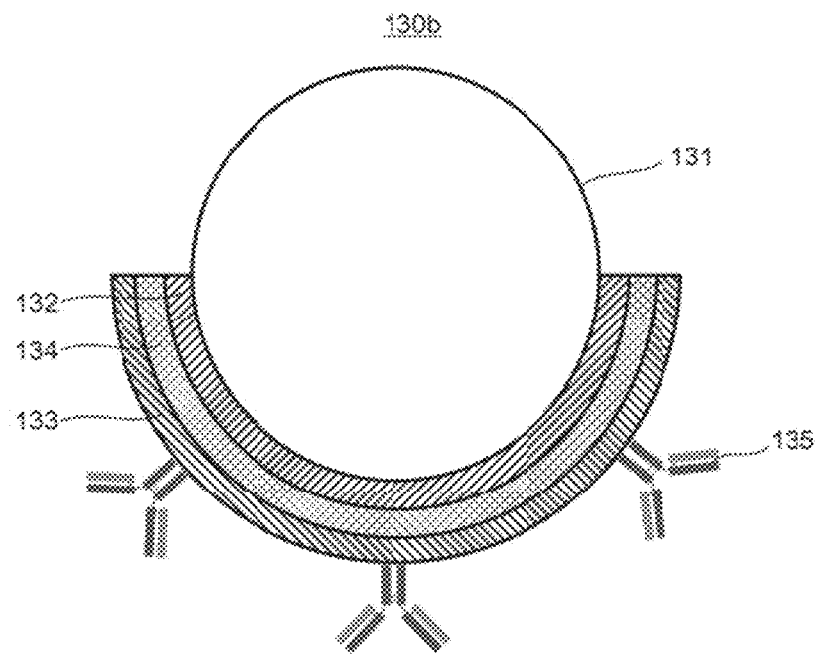
[FIG. 4]
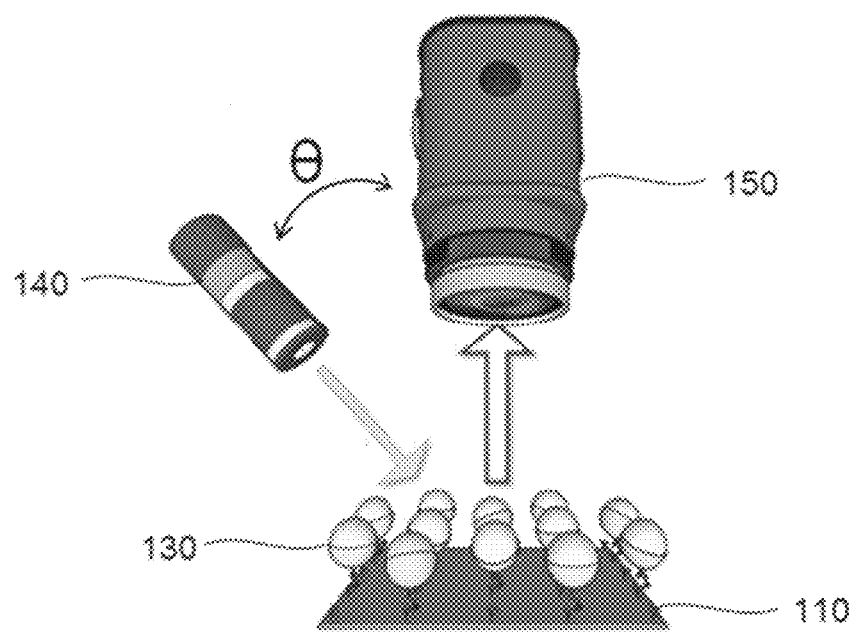

[FIG. 5]
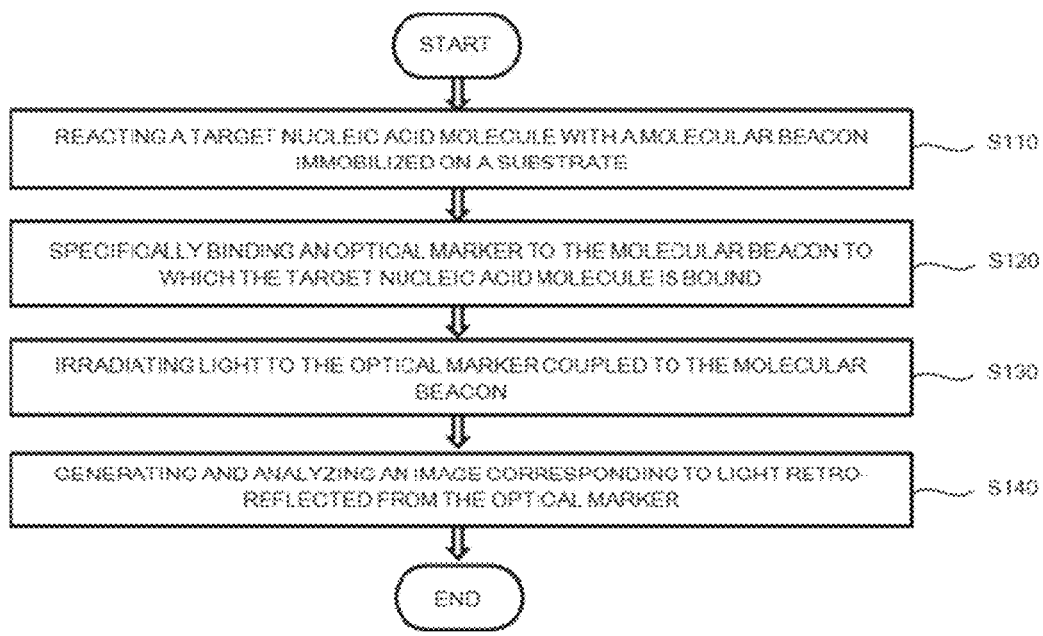

FIG. 6
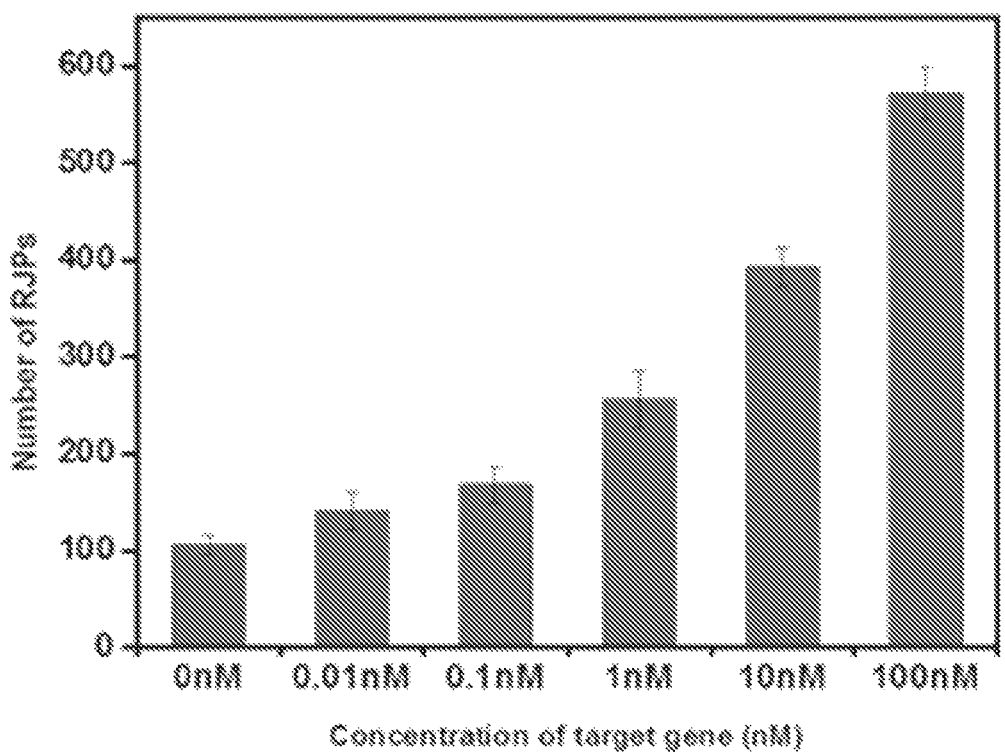
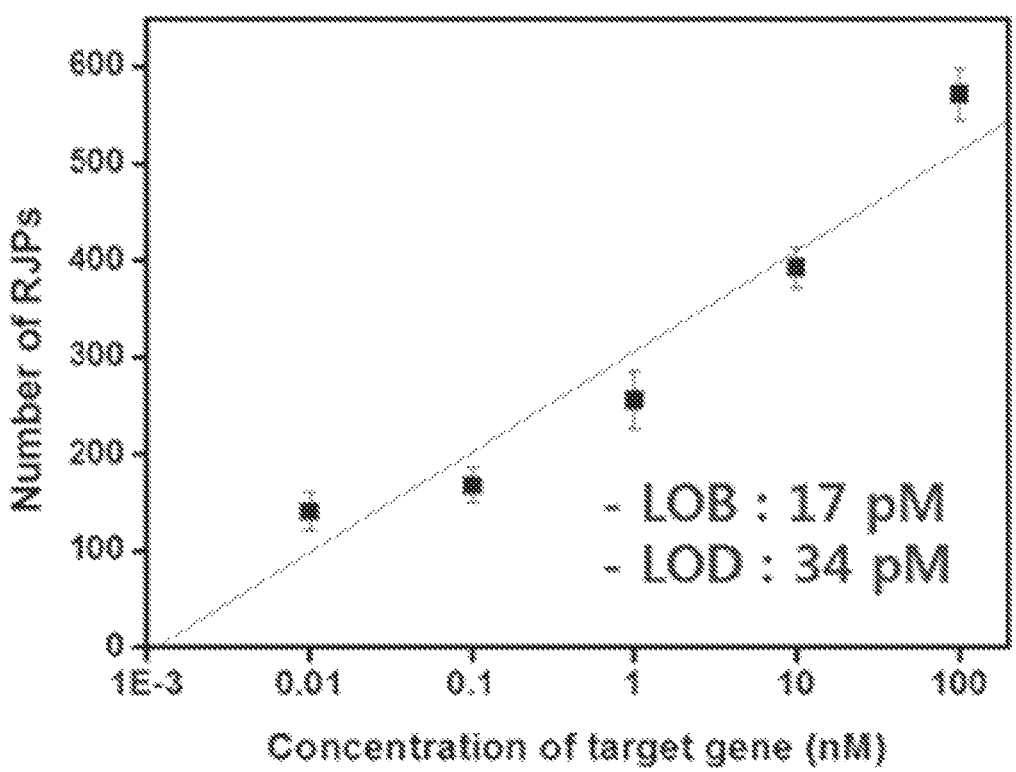

[FIG. 7]
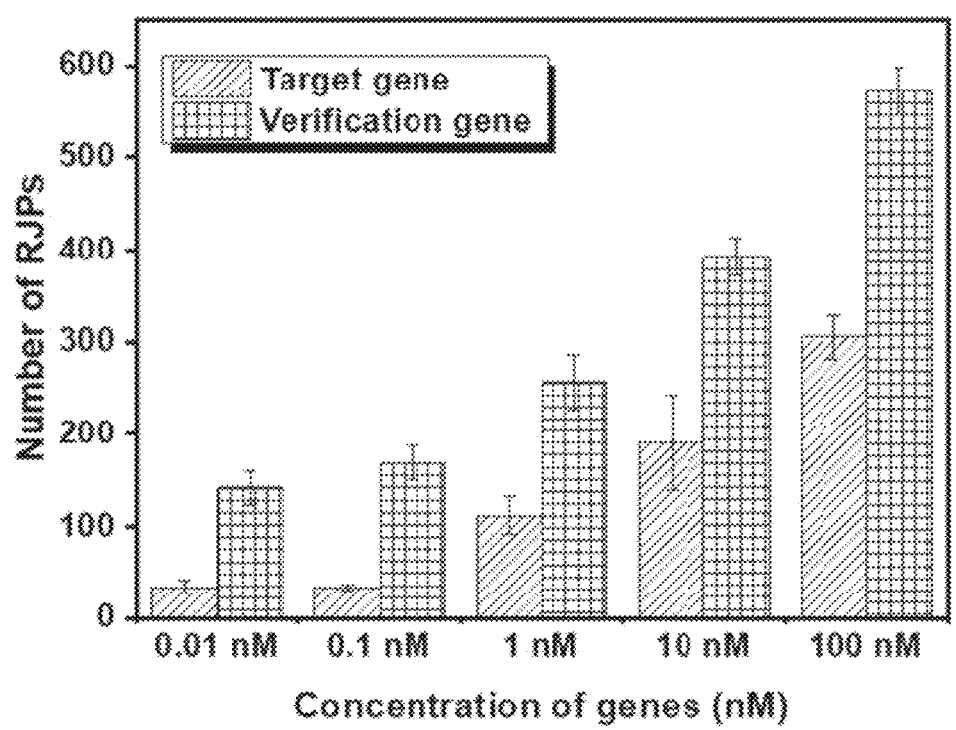

MOLECULAR BEACON-BASED OPTICAL GENE BIOSENSOR EMPLOYING RETRO-REFLECTION AND QUANTITATIVE ANALYSIS METHOD OF NUCLEIC ACID MOLECULE

CROSS-REFERENCE TO RELATED APPLICATION

This application is a National Stage of International Application No. PCT/KR2018/002812 filed Mar. 9, 2018, claiming priority based on Korean Patent Application No. 10-2017-0053397 filed on Apr. 26, 2017, on the Korean Intellectual Property Office, the entire disclosure of which is incorporated herein by reference for all purposes.

BACKGROUND

1. Field

The present disclosure relates to an optical gene biosensor capable of quantitative analysis of a target nucleic acid molecule using an optical scheme and an analytical method using the same.

2. Description of Related Art

The molecular beacon refers to an oligonucleotide with a stem-loop structure with self-complementary sections. The beacon includes a stem section positioned at each of both ends thereof and having a self-complementary sequence, and a loop section between the two stem sections and having a complementary sequence to a nucleic acid molecule (DNA, RNA, etc.) to be detected.

In a conventional biosensor using the molecular beacon, typically, one end of the oligonucleotide is modified with a fluorophore, while the other end thereof is modified with a quencher which can absorb and quench fluorescence derived from the fluorophore.

When no target nucleic acid molecule is present, the stem sections with the self-complementary sequences hybridize with each other, and thus the molecular beacon exhibits a hairpin structure. In this structure, the fluorophore and the quencher defining both distal ends of the molecular beacon are adjacent to each other. As a result, the fluorescence from the fluorophore is transferred to the quencher via fluorescence resonance energy transfer and thus is quenched. In contrast, when a complementary target nucleic acid molecule is present, the target nucleic acid molecule is hybridized with the loop section of the molecular beacon to form a double helix structure. As a result, a torsional force acts to separate the stem sections of the molecular beacon from each other. As a result, a distance between the fluorophore and the quencher becomes larger, such that the energy transfer phenomenon between the fluorophore and the quencher is eliminated, and thus a fluorescence signal unique to the fluorophore is emitted. Since an intensity of the fluorescence signal emitted under this condition is proportional to a concentration of the target nucleic acid molecule, presence or absence of the target nucleic acid molecule or the concentration thereof can be quantitatively/quantitatively analyzed by tracking the fluorescence signal change.

As described above, the conventional molecular beacon-based biosensor may use the fluorophore. Thus, spectroscopy-based fluorescence analysis equipment is required.

Specifically, since the fluorophore provides a valid signal only related to excitation light having a particular wavelength, the conventional biosensor uses essentially a combination of a halogen lamp that provides all wavelengths as a light source and a monochromator that can select and irradiate light having a specific wavelength from the all wavelengths. Alternatively, the conventional biosensor uses essentially a high power laser device and LEDs for supplying laser having short wavelengths. In this case, since these light sources are very expensive and require high power consumption, it may be difficult to miniaturize, carry and commercialize the biosensor.

Further, according to the conventional biosensor, an emission filter is required to specifically detect and separate the excitation light irradiated with the fluorescent signal derived from the fluorophore. In this connection, expensive light receiving equipment such as a photomultiplier tube (PMT) is essential for sensitive detection of the fluorescence signal. In addition, there is a problem that a very sophisticated arrangement and assembly between these optical components is required.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

One purpose of the present disclosure is to provide an optical gene biosensor that is capable of detecting presence, a concentration, and the like of a target nucleic acid molecule in a non-spectral manner using a retro-reflective optical marker.

Another purpose of the present disclosure is to provide a method for performing quantitative analysis of a target nucleic acid molecule using the optical gene biosensor.

Purposes of the present disclosure are not limited to the above-mentioned purpose. Other purposes and advantages of the present disclosure as not mentioned above may be understood from following descriptions and more clearly understood from embodiments of the present disclosure. Further, it will be readily appreciated that the purposes and advantages of the present disclosure may be realized by features and combinations thereof as disclosed in the claims.

A first aspect of the present disclosure proposes an optical gene biosensor comprising: a substrate; a molecular beacon anchored to the substrate, wherein the molecular beacon includes an oligonucleotide specifically binding to a target nucleic acid molecule and a first compound bound to a first terminal of the oligonucleotide; an optical marker specifically binding to the first compound, wherein the optical marker is configured to retro-reflect irradiated light; a light source for irradiating the optical marker with light; and a light-receiver for receiving light retro-reflected from the optical marker.

In one implementation of the first aspect, the oligonucleotide includes: a loop section having base sequences complementary to base sequences of the target nucleic acid molecule; a first stem section extending from a first terminal of the loop section and having a terminal coupled to the first compound; and a second stem section extending from a second terminal of the loop section opposite to the first terminal of the loop section and having base sequences complementary to base sequences of the first stem section, wherein the second stem is bound to the substrate.

In one implementation of the first aspect, the loop section includes 20 to 40 base sequences, wherein each of the first and second stem sections includes 4 to 8 base sequences.

In one implementation of the first aspect, the first compound includes at least one selected from a group consisting of biotin, dinitrophenyl (DNP), and digoxigenin (DIG).

In one implementation of the first aspect, the molecular beacon further includes a first spacer compound connecting the first compound to a terminal of the first stem section, wherein the first spacer compound includes an alkyl chain having 4 to 10 carbons or mini-poly(ethylene glycol) having about 4 to 10 repeating units.

In one implementation of the first aspect, the molecular beacon further includes a functional group covalently bonding to the substrate.

In one implementation of the first aspect, the molecular beacon further includes a second spacer compound connecting the functional group to a terminal of the second stem section, wherein the second spacer compound includes an alkyl chain having 4 to 10 carbons or mini-poly(ethylene glycol) having about 4 to 10 repeating units.

In one implementation of the first aspect, the optical marker includes: a transparent core particle; a total-reflection inducing layer to cover a portion of a surface of the core particle, wherein the total-reflection inducing layer is made of a material having a refractive index lower than a refractive index of the core particle in a visible light wavelength range of 360 nm to 820 nm; a to-be-modified layer formed on the total-reflection inducing layer; and a second compound coupled to the to-be-modified layer, wherein the second compound specifically binds to the first compound.

In one implementation of the first aspect, the core particle is made of one selected from a group consisting of silica, glass, polystyrene, and polymethyl methacrylate having a refractive index of 1.4 or greater in the visible wavelength range.

In one implementation of the first aspect, the total-reflection inducing layer is made of at least one selected from a group consisting of aluminum (Al), copper (Cu), gold (Au), silver (Ag), and zinc (Zn).

In one implementation of the first aspect, the core particle has an average diameter of 600 nm or greater and 2 µm or smaller, wherein the total-reflection inducing layer covers 30% to 70% of the surface of the core particle.

In one implementation of the first aspect, the total-reflection inducing layer has a thickness of 10 to 100 nm.

In one implementation of the first aspect, the to-be-modified layer is made of at least one selected from a group consisting of platinum (Pt), gold (Au), and silver (Ag).

In one implementation of the first aspect, the first compound includes at least one selected from a group consisting of biotin, dinitrophenyl (DNP), and digoxigenin (DIG), wherein when the first compound includes the biotin, the second compound includes at least one selected from a group consisting of avidin, streptavidin and neutraavidin specifically binding to the biotin, wherein when the first compound includes the dinitrophenyl, the second compound includes an anti-DNP antibody compound specifically binding to the dinitrophenyl (DNP), wherein when the first compound includes the digoxigenin (DIG), the second compound includes an anti-DIG antibody compound specifically binding to the digoxigenin (DIG).

In one implementation of the first aspect, the optical marker further includes a magnetic layer made of magnetic material, wherein the magnetic layer is placed between the total-reflection inducing layer and the to-be-modified layer.

In one implementation of the first aspect, the light-source is placed above the optical marker, and irradiates the optical marker with mixed light of a plurality of wavelengths or light of a single wavelength, wherein the light-receiver is placed above the optical marker and is spaced apart from the light-source, wherein the light-receiver receives light generated from the light-source and then irradiated to the optical marker and then retro-reflected from the optical marker.

In one implementation of the first aspect, the light-source emits light in an inclined manner in a range of 0° exclusive to 45° inclusive with respect to a propagating direction of the retro-reflected light.

In one implementation of the first aspect, the light-receiver includes: an image generator for receiving the retro-reflected light and for imaging the light into an image signal; and an image analyzer for analyzing the image signal generated from the image generator.

In one implementation of the first aspect, the image analyzer counts a number of the optical markers based on the image signal and analyzes a concentration of the target nucleic acid molecule based on the number.

In one implementation of the first aspect, the image analyzer measures an amount of light retro-reflected from the optical marker based on the image signal, and analyzes a concentration of the target nucleic acid molecule based on the amount.

A second aspect of the present disclosure proposes a method for quantitatively analyzing a nucleic acid molecule, the method comprising: a first step of reacting a target nucleic acid molecule with a molecular beacon immobilized on a substrate; a second step of specifically binding an optical marker to the molecular beacon to which the target nucleic acid molecule is bound; a third step of irradiating light to the optical marker coupled to the molecular beacon; and a fourth step of generating and analyzing an image corresponding to light retro-reflected from the optical marker.

In one implementation of the second aspect, the first step includes: applying a solution sample containing the target nucleic acid molecule onto the substrate to which the molecular beacon is immobilized; and reacting the target nucleic acid molecule with a loop section of the molecular beacon, wherein the loop section has base sequences complementary to base sequences of the target nucleic acid molecule.

In one implementation of the second aspect, the second step includes: applying the optical markers onto the substrate on which the solution sample is present; and specifically binding the optical markers to the molecular beacon to which the target nucleic acid molecule is bound.

In one implementation of the second aspect, the method further comprises, after the second step and before the third step, removing non-reacted optical markers not bound to the molecular beacon.

In one implementation of the second aspect, in the third step, white light is irradiated to the optical marker, wherein in the fourth step, quantitative analysis of the target nucleic acid molecule is performed based on an image corresponding to retro-reflected white light.

Effects of the present disclosure are as follows but are not limited thereto.

According to the present disclosure, after binding the target nucleic acid molecule to the molecular beacon, the optical marker is bound to the molecular beacon. Thus, the quantitative analysis of the target nucleic acid molecule is performed using light retro-reflected from the optical marker. Thus, the target nucleic acid molecule can be quantitatively analyzed at a high sensitivity without use of expensive and bulky optical equipment, compared to the conventional biosensor using the fluorophore.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

FIG. 1 is a schematic diagram for describing an optical gene biosensor according to an embodiment of the present disclosure.

FIG. 2 is a schematic view for describing a molecular beacon shown in FIG. 1.

FIGS. 3A and 3B are cross-sectional views for describing an optical marker shown in FIG. 1.

FIG. 4 is a schematic diagram for describing a positional relationship between a light-source and a light-receiver shown in FIG. 1.

FIG. 5 is a flow chart to describe a method of quantitative analysis of a nucleic acid molecule according to an embodiment of the present disclosure.

FIG. 6 is a graph showing a result of gene analysis according to Present Example 2.

FIG. 7 is a graph showing the results of gene analysis according to Present Example 2.

DETAILED DESCRIPTIONS

For simplicity and clarity of illustration, elements in the figures. are not necessarily drawn to scale. The same reference numbers in different figures. denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "includes", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic diagram for describing an optical gene biosensor according to an embodiment of the present disclosure. FIG. 2 is a schematic view for describing a molecular beacon shown in FIG. 1. FIG. 3A and FIG. 3B are cross-sectional views for describing an optical marker shown in FIG. 1. FIG. 4 is a schematic diagram for describing a positional relationship between a light-source and a light-receiver shown in FIG. 1.

Referring to FIG. 1 to FIG. 4, an optical gene biosensor 100 according to an embodiment of the present disclosure may quantitatively analyze a target nucleic acid molecule 10 to be detected in an optical manner. In one embodiment, the optical gene biosensor 100 may include a molecular beacon 110, a substrate 120, an optical marker 130, a light-source 140, and a light-receiver 150.

The molecular beacon 110 may include an oligonucleotide 111 that specifically binds to a target nucleic acid molecule 10 and a first compound 112 that specifically binds to the optical marker 130.

The oligonucleotide 111 may include a loop section 111*a*, a first stem section 111*b*, and a second stem section 111*c*.

The loop section 111*a* may specifically bind to the target nucleic acid molecule 10. For example, the loop section 111*a* may have a base sequence complementary to the target nucleic acid molecule 10 and thus hybridize with the target gene 10. In one embodiment, the loop section 111*a* may include about 20 to about 40 base sequences in consideration of base sequences of the target nucleic acid molecule 10.

The first stem section 111b may include a plurality of first base sequences extending from a first terminal of the loop section 111a. The second stem section 111c may include a plurality of second bases extending from a second terminal of the loop section 111a opposite the first terminal. The first base sequences of the first stem section 111b may be complementary to the second base sequences of the second stem section 111c. Thus, when the target nucleic acid molecule 10 is not bound to the loop section 111a, the oligonucleotide 111 may have a hairpin structure in which the first and second stem sections 111b and 111c are hybridized with each other, as shown on a left side of FIG. 2. In one embodiment, each of the first and second stem sections 111b and 111c may include about 4 to 8 complementary base sequences.

A terminal of the first stem section 111b may be coupled to the first compound 112. A terminal of the second stem section 111c may be fixed to the substrate 120. This will be described later.

The first compound 112 may be coupled to the terminal of the first stem section 111b and may be specifically combined with the optical marker 130. Specifically, when the first and second stem sections 111b and 111c are hybridized with each other, the optical marker 130 cannot bind to the first compound 112 due to steric hindrance. However, when the target nucleic acid molecule 10 hybridizes with the loop section 111a, the hybridization between the first and second stem sections 111b and 111c is disabled, such that the optical marker 130 may be coupled to the first compound 112.

The first compound 112 is not limited to a specific type as long as the compound 112 can specifically bind to a specific compound of the optical marker 130. In one embodiment, the first compound 112 may include a ligand molecule. For example, the first compound 112 may include one or more selected from a group consisting of biotin, dinitrophenyl (DNP), digoxigenin (DIG), and the like.

In one embodiment, the first compound 112 may be coupled to the terminal of the first stem section 111b via a first spacer compound 114. That is, the first compound 112 may be coupled to one terminal of the first spacer compound 114, while the other terminal of the first spacer compound 114 may be coupled to the terminal of the first stem section 111b. Otherwise, the first compound 112 may be directly bonded to the terminal of the first stem section 111b. In this case, structural and steric hindrance caused by the molecular beacon 110 may reduce a bond yield between the first compound 112 and a second compound 135 of the optical marker 130. However, when coupling the first compound 112 to the terminal of the first stem section 111b via the first spacer compound 114, the first compound 112 is spaced further away from the substrate 120 due to the presence of the first spacer compound 114. Thus, not only the first compound 112 may be exposed to a sample solution containing the target nucleic acid molecule 10 but also fluidity thereof in the sample solution is improved, thereby to improve the bond yield between the first compound 112 and the second compound 135 of the optical marker 130.

In one embodiment, the first spacer compound 114 may include an alkyl chain having about 4 to 10 carbons or mini-poly(ethylene glycol) having about 4 to 10 repeating units.

In one example, the terminal of the second stem section 111c may be modified with a functional group 113 to be fixed to the substrate 120. The functional group 113 is not limited to a specific type as long as the functional group 113 forms a chemical bond with the substrate 120 to fix the molecular beacon 110 to the substrate 120. For example, the functional group 113 may include an amine group —$NH_2$. In one embodiment, the functional group 113 may be coupled to the terminal of the second stem section 111c via a second spacer compound 115. When the molecular beacon 110 includes the second spacer compound 115, the oligonucleotide 111 may be spaced farther away from the substrate 120 and thus may be exposed to the sample solution containing the target nucleic acid molecule 10 as well as may have improved flow ability in the sample solution, thereby improving the hybridization yield between the loop section 111a of the oligonucleotide 111 and the target nucleic acid molecule 10. Further, the second spacer compound 115 may act in a similar manner to the first spacer compound 114 to improve the bond yield between the first compound 112 and the second compound 135 of the optical marker 130.

In one embodiment, the second spacer compound 115 may include an alkyl chain having about 4 to 10 carbons or about 4 to 10 repeating units-containing mini-poly(ethylene glycol).

The substrate 120 is not limited to a specific type as long as the molecular beacon 110 may be fixed thereto. For example, the substrate 120 may be made of glass, silicon, polymer, metal, etc., and may have a flat top surface to which the molecular beacon 110 is bonded. The polymer may include polystyrene (PS), polymethyl methacrylate (PMMA), olefin copolymer (COC), polydimethylsiloxane (PDMS), etc. The metal may include noble metals such as gold (Au), platinum (Pt), and silver (Ag).

In one embodiment, when the substrate 120 is made of one of a glass, a silicone, polymer and the functional group 113 of the molecular beacon 110 is an amine group, the surface of the substrate 120 may be activated by a plasma treatment or ultraviolet light exposure thereto, and then 3-aminopropyltriethoxysilane (APTES) is applied to the active surface thereof to expose the amine group. Subsequently, an amine reactive crosslinker such as glutaraldehyde is applied thereto. This may cause covalent bonding between the amine group which is a functional group of the molecular beacon 110 and an amine group of the 3-aminopropyltriethoxysilane. In this way, the molecular beacon 110 may be fixed to the substrate 120.

In another embodiment, when the substrate 120 is made of a noble metal and the functional group 113 of the molecular beacon 110 is an amine group, an amine-reactive self-assembled monolayer (SAM) is formed using a material such as DTSSP (3,3'-dithiobis(sulfosuccinimidyl propionate) or DTSP (dithiobis(succinimidyl propionate) to expose a succinimide group on the surface of the substrate 120. Then, the amine functional group 113 of the molecular beacon 110 and the succinimide group may be covalently bonded to each other via an amide bond. In this way, the molecular beacon 110 may be fixed to the substrate 120.

In one example, in the two cases, after combining the molecular beacon 110 to the substrate 120, a molecule including an amine group such as ethanolamine may be used to block reaction residues remaining on the surface of the substrate, such as aldehyde or succinimide group.

The optical marker 130 may specifically bind to the first compound of the molecular beacon 110 and may retroreflect the light emitted from the light-source 140 toward the light-source 140.

In one embodiment, as shown in FIG. 3a, the optical marker 130 may include a transparent core particle 131, a total-reflection inducing layer 132 covering a portion of the transparent core particle 131, a to-be-modified layer 133 disposed on the total-reflection inducing layer 132, and a second compound 135 coupled directly or indirectly to the to-be-modified layer 133.

The core particle 131 may have a spherical shape. As used herein, the term 'spherical' means not only a perfect sphere with the same radius from a center to every point on a surface thereof but also an actual sphere whose difference between a maximum radius and a minimum radius is smaller than about 10%.

In one embodiment, the core particle 131 may have an average diameter of about 600 nm or greater and 2 µm or smaller, in consideration of a relationship between the diameter and a wavelength of light emitted from the light-source 140, bio sensing ability, and the like.

In one embodiment, the core particle 131 may be made of a transparent material that may transmit incident light. For example, the core particle 131 may be made of a transparent oxide, a transparent polymer material, or the like. The transparent oxide may include, for example, silica, glass, etc. The transparent polymer material may include, for example, polystyrene, poly methyl methacrylate, and the like.

The total-reflection inducing layer 132 may be formed to cover a portion of the surface of the core particle 131 and may totally reflect at least a portion of light traveling inside the core particle 131 to increase an amount of light as retro-reflected toward the light-source 140.

In one embodiment, the total-reflection inducing layer 132 may be formed on the surface of the core particle 131 to cover an area of at least about 30% and at most 70% of the surface of the core particle 131. When the total-reflection inducing layer 132 covers an area smaller than 30% of the surface of the core particle 131, there is a problem that a sensitivity of the gene biosensor 100 is deteriorated since a large amount of the light incident inside the core particle 131 is not retro-reflected but is leaked. To the contrary, when the total-reflection inducing layer 132 covers an area greater than 70% of the surface of the core particle 131, there may be a problem that the sensitivity of the gene biosensor 100 is reduced since the amount of light incident to the core particle 131 decreases. Thus, in one embodiment, the total-reflection inducing layer 132 may be formed on the surface of the core particle 131 to cover at least about 40% or at most 60% of the surface of the core particle 131.

In one embodiment, to totally reflect at least a portion of the light propagating inside the core particle 131 to increase the amount of light retro-reflected toward the light-source 140, the total-reflection inducing layer 132 may be made of a material with a lower refractive index than that of the core particle 131. In one embodiment, the core particle 131 may be made of a material having a refractive index of at least about 1.4 in a visible wavelength range of at least 360 nm to 820 nm, while the total-reflection inducing layer 132 may be made of a material having a refractive index lower than that of the core particle 131. Specifically, when the core particle 131 is made of a transparent oxide or transparent polymer material having a refractive index of about 1.4 or greater in the visible region, the total-reflection inducing layer 132 may be made of a metallic material having a refractive index lower than 1.4. For example, the total-reflection inducing layer 132 may be made of at least one selected from gold (Au) having a refractive index of about 0.22 with respect to light at a wavelength of 532 nm, silver (Ag) having a refractive index of about 0.15 with respect to light at a wavelength of 532 nm, aluminum (Al) having a refractive index of about 1.0 with respect to light at a wavelength of 532 nm, copper (Cu) with a refractive index of about 0.4 with respect to light at a wavelength of 532 nm, zinc (Zn) with a refractive index of about 1.2 with respect to light at a wavelength of 532 nm.

In one embodiment, to improve adhesion between the total-reflection inducing layer 132 and the core particle 131, chromium (Cr) may be applied to the surface of the core particle 131 and then the total-reflection inducing layer 132 may be formed thereon. In this case, in order to prevent retro-reflection ability from deteriorating, the chromium is preferably applied at a thickness of about 2 nm to 5 nm. Alternatively, in another embodiment, the total-reflection inducing layer 132 itself may be made of a material that is highly adhesive with the core particle 131. For example, when the core particle 131 is made of a transparent oxide, the total-reflection inducing layer 132 may be made of aluminum (Al) or copper (Cu).

In one embodiment, the total-reflection inducing layer 132 may have a thickness of about 10 to 100 nm to prevent light leakage due to light transmission and to improve dispersibility of the optical marker 130. When the thickness of the total-reflection inducing layer 132 is smaller than 10 nm, a portion of the light incident inside the core particle 131 may pass through the total-reflection inducing layer 132 and may leak. When the thickness of the total-reflection inducing layer 132 exceeds 100 nm, a weight of the optical marker 130 may increase, resulting in a decrease in the dispersibility of the optical marker 130 in the liquid.

The to-be-modified layer 133 may be formed on the surface of the total-reflection inducing layer 132. The to-be-modified layer 133 may be made of a metallic material that can be easily combined with biological substances. For example, the to-be-modified layer 133 may be made of noble metals such as platinum (Pt), gold (Au), silver (Ag), etc., which are easily modified with biological substances and have excellent anti-oxidation ability.

In one embodiment, the to-be-modified layer 133 may be formed as a separate layer independent of the total-reflection inducing layer 132. For example, when the total-reflection inducing layer 132 may be made of a metal material other than noble metals, while the to-be-modified layer 133 may be made of a noble metal material layer covering the total-reflection inducing layer 132.

Alternatively, in another embodiment, the to-be-modified layer 133 and the total-reflection inducing layer 132 may be integrally formed with each other. For example, when the total-reflection inducing layer 132 is made of noble metals with a lower refractive index than that of the core particle, such as gold (Au) or silver (Ag), the total-reflection inducing layer 132 may function as the to-be-modified layer 133.

In one embodiment, the to-be-modified layer 133 may have a thickness of about 100 nm or smaller to prevent the dispersibility decrease, and thus aggregation within the liquid of the optical marker 130.

The second compound 135 may be bonded directly or indirectly to the to-be-modified layer 133 and may bind specifically to the first compound 112 of the molecular beacon 110. A type of the second compound 135 may vary depending on the first compound 112. The second compound 135 may include one or more selected from proteins, nucleic acids, ligands, and the like. For example, when the first compound 112 of the molecular beacon 110 includes a biotin, the second compound 135 may include one or more protein compounds selected from avidin, streptavidin, neutravidin, etc., which may specifically bind to the biotin. In another example, when the first compound 112 of the molecular beacon 110 includes dinitrophenyl (DNP), the second compound 135 may include an anti-DNP antibody compound that may specifically bind to the dinitrophenyl (DNP). In another example, when the first compound 112 of the molecular beacon 110 includes digoxigenin (DIG), the second compound 135 may include an anti-DIG antibody compound that may bind to the digoxigenin (DIG).

In one example, the second compound 135 may be bound only to a surface of the to-be-modified layer 133 and may not bond to an exposed surface of the core particle 131. Thus, when specifying a location of the second compound 135 with respect to the core particle 131 coated by the total-reflection inducing layer 132 and the to-be-modified layer 133, an exposed portion of the core particle 131 is directed to the light-source 140 when the maker 130 is bound to the molecular beacon 110, thereby inducing a more powerful retro-reflective signal. As a result, the sensitivity of the gene biosensor 100 can be significantly improved.

In one embodiment of the present disclosure, as shown in FIG. 3b, the optical marker 130 may further include a magnetic layer 134 made of a magnetic material and disposed between the total-reflection inducing layer 132 and the to-be-modified layer 133. The magnetic layer 134 may be made of a magnetic material such as, for example, iron (Fe), nickel (Ni), manganese (Mn), fired bodies or oxides thereof. When the optical marker 130 further includes the magnetic layer 134, a magnetic field may be externally applied thereto, such that an orientation of the optical marker 130 may be adjusted to not only induce a more powerful retro-reflective signal, but also the external magnetic field may be used to remove optical markers 130 which are not combined with the molecular beacon 110.

The light-source 140 may be placed above the optical marker 130. The optical marker 130 coupled to the molecular beacon 110 may be irradiated with light from the light source. A light source type of the light-source 140 is not limited to a specific type. For example, the light source type of the light-source 140 may include a light source type for generating light in which light-beams of various wavelengths are mixed, or a light source type for generating monochromatic light of a specific wavelength. Specifically, the light source type of the light-source 140 may include a halogen lamp, a mercury lamp, a fluorescent lamp, a light emitting diode (LED), or a laser. However, the present disclosure is not limited thereto.

The light-receiver 150 may be placed above the optical marker 130 and be spaced apart from the light-source 140. The light-receiver 150 may receive the light emitted from the light-source 140 and irradiated to the optical marker 130 and then retro-reflected from the optical marker 130 and may quantitatively analyze information about the presence or absence and concentration of the target nucleic acid molecule 10 based on the received light. As long as the light receiver 150 could receive the retro-reflected light and analyze the information about the target nucleic acid molecule 10 based on the retro-reflected light, a configuration of the light-receiver 150 is not particularly limited. In one embodiment, the light-receiver 150 may include an image generator for imaging the retro-reflected optical signal and an image analyzer for analyzing image information generated by the image generator. In this case, the image generator may include any known image generating device such as a digital camera without limitation. As the image analyzer, a known image analysis system may be used without limitation.

In one embodiment, the light-receiver 150 may quantify the concentration of the target nucleic acid molecule 10 by the image analyzer counting the number of the optical markers 130 based on the image generated by the image generator.

In another embodiment, the light-receiver 150 may quantify the concentration of the target nucleic acid molecule 10 by the image analyzer measuring the amount of light retro-reflected from the optical marker 130 based on the image produced by the image generator.

In one embodiment, as shown in FIG. 4, to minimize the degradation of the sensitive due to interference between the light irradiated from the light-source 140 and the retro-reflected light from the optical marker 130, and to prevent degradation of the sensitivity due to light mirror-reflected from the substrate 120, the light-receiver is oriented to receive retro-reflected light within an angle range of about −10° to +10° relative to a normal line to a surface of the substrate 121 while the light-source 140 is oriented to irradiate light in an inclined manner at an angle of about 0° exclusive to 45° inclusive with respect to an advancing direction of the retro-reflected light.

FIG. 5 is a flow chart for describing the quantitative analysis method of nucleic acid molecule according to an embodiment of the present disclosure. The quantitative analysis method of the nucleic acid molecule according to an embodiment of the present disclosure may be performed using the optical gene biosensor 100 as described with reference to FIGS. 1 to 4.

Referring to FIG. 5 along with FIG. 1 to FIG. 4, the quantitative analysis method of the nucleic acid molecule according to an embodiment of the present disclosure includes a first step S110 of reacting the target nucleic acid molecule 10 with the molecular beacon 110 immobilized on the substrate 120; a second step S120 of specifically coupling the optical marker 130 to the molecular beacon 110 to which the target nucleic acid molecule 10 is bound; a third step S130 of irradiating light to the optical marker 130 coupled to the molecular beacon 110; and a fourth step S140 of generating and analyzing an image of the retro-reflected light from the optical marker 130.

In the first step S110, a solution sample containing the nucleic acid molecule 10 is applied onto the substrate 120 to which the molecular beacon 110 is immobilized. Thus, the step S110 may combine the loop section 111a of the molecular beacon 110 with the nucleic acid molecule 10. As previously described, the loop section 111a has a base sequence complementary to a base sequence of the nucleic acid molecule 10 and thus may specifically bind to the nucleic acid molecule. To facilitate the binding between the molecular beacon 110 and the nucleic acid molecule 10, the solution sample containing the nucleic acid molecule 10 may be heated to a temperature of about 35° C. to 45° C. However, the heating temperature may vary depending on a length of the base sequence of each of the molecular beacon 110 and the target nucleic acid molecule 10 and percentages of guanine (G) and cytosine (C) present in the base sequence.

In one example, after the solution sample containing the nucleic acid molecule 10 is applied onto the substrate 120 to induce the binding of the molecular beacon 110 to the nucleic acid molecule 10, the solution sample may be cooled to about 1 to 5° C. for a predetermined time duration and then maintained at room temperature in order to convert molecular beacons 110 non-reacted with the nucleic acid molecule 10 to a hairpin structure.

In the second step S120, the optical markers 130 may be applied onto the substrate 120 on which the solution sample is present to specifically couple the optical markers 130 to the molecular beacon 110 to which the target nucleic acid molecule 10 is bound. In this case, the first compound 112 of the molecular beacon 110 may bind to the second compound 135 of the optical marker 130 in a specific manner.

As described above, the oligonucleotide 111 of each of the molecular beacons 110 has the first and second stem sections 111b and 111c formed at both terminals of the loop section 111a respectively and having complementary base sequences with each other. Thus, the oligonucleotide 111 bound to the nucleic acid molecule 10 maintains a linear structure in which the terminal thereof coupled to the first compound 112 becomes a top terminal away from the substrate 120. To the contrary, in the oligonucleotide 111 to which the nucleic acid molecule 10 is not bound, the first and second stem sections 111b and 111c bind to each other such that the oligonucleotide has a hairpin structure. As a result, the terminal thereof coupled to the first compound 112 may face the substrate 120. Thus, when applying the optical markers 130 on the substrate 120 where the solution sample is present, the optical markers 130 may be readily accessible to the first compound 112 of the linear oligonucleotide 111 to form a bond 135 between the first compound 112 of the oligonucleotide 111 and the second compound of the optical marker 130. However, the first compound 112 of the oligonucleotide 111 with the hairpin structure may have difficulty in accessing to the optical marker 130 due to the steric hindrance. As a result, the bond between the first compound 112 of the oligonucleotide 111 and the second compound 135 of the optical marker 130 may not occur.

In one example, after coupling the optical marker 130 to the molecular beacon 110 to which the target nucleic acid molecule 10 is bound, the optical markers 130 as non-reacted with the beacon may be removed. The removal of the non-reacted optical markers 130 may be performed using a washing solution to remove a solvent of the solution sample and other non-reacted materials.

In the third step 130, the light-source 140 may be used to irradiate the optical marker 130 coupled to the molecular beacon 110 with light. In this case, the second compound 135 of the optical marker 130 is bound only to the to-be-modified layer 133 surface and not to the exposed surface of the core particle 131. Thus, when the optical marker 130 is bound to the molecular beacon 110, the exposed surface of the core particle 131 of the optical marker 130 is oriented toward the light-receiver 150. As a result, the receiver 150 may generate a stronger retro-reflective signal in response to the light irradiation from the light-source 140.

In the fourth step 140, the light-receiver 150 generates and analyzes an image of the substrate 120 to which the optical marker 130 is coupled, while the light-source 140 illuminates light. For example, the light-receiver 150 may generate an image of the substrate 120 using the image generator. The image may be analyzed by the image analyzer counting the number of the optical markers 130 based on the image.

According to the present disclosure, after binding the target nucleic acid molecule to the molecular beacon, the optical marker is bound to the molecular beacon. Thus, the quantitative analysis of the target nucleic acid molecule is performed using light retro-reflected from the optical marker. Thus, the target nucleic acid molecule can be quantitatively analyzed at a high sensitivity without use of expensive and bulky optical equipment, compared to the conventional biosensor using the fluorophore.

Hereinafter, Present Examples of the present disclosure will be described in detail. The following Present Examples are only some embodiments of the present disclosure, and the present disclosure should not be construed as limited to the following Examples.

Present Example 1

To demonstrate applicability of the molecular beacon-based gene bio-sensing scheme using the retro-reflection principle developed in accordance with the present disclosure to actual nuclear acid marker measurement and to verify analytical capability thereof, gene sensing of a FemA gene of antibiotic-resistant Staphylococcus aureus as an infectious microorganism was performed. Specifically, a cDNA fragment of a FemA gene having a base sequence of 5'-CTATGAGTTAAAGCTTGCTGAAGGTTATGA (SEQ ID NO: 1)-3' was synthesized and employed as a target nucleic acid molecule.

The molecular beacon structure was designed to have 5'-$NH_2$-$(CH_2)_6$-GTGAGCTCAT-AACCTTCAGCAAGCTTTAACTCATAGGCTCAC (SEQ ID NO: 2) -$(CH_2)_6$-Biotin-3'. The molecular beacon has a stem section including 6×2 base pairs (bps) and a loop section including 30 base pairs (bps).

As a substrate on which the molecular beacon is fixed, a chip for particle counting in which a gold thin film is patterned on a glass substrate is used. Specifically, the gold thin film pattern was formed such that 16 squares, each having an area of 340 μm×340 μm, are patterned.

The surface of the gold thin film pattern on which the amine reactive SAM was formed using DTSSP was modified with the molecular beacons. Then, CDNA fragments of the FemA gene at various concentrations of 0 nM, 0.01 nM, 0.1 nM, 1.0 nM, 10.0 nM and 100 nM were reacted with the molecular beacons. Subsequently, optical marker particles modified with streptavidin that specifically bind to the biotin of the molecular beacon are bound to the molecular beacons. Then, the optical marker particles were irradiated with white light using a white LED light source. At this state, an image of the substrate was generated using a digital camera connected to an objective lens having a numerical aperture of 0.065. The image was then analyzed by counting the number of the optical marker particles using the Image J program.

Experimental Example 1

FIG. 6 is a graph showing a result of gene analysis according to Present Example 1. This graph indicates an average of three repeated experiment results.

Referring to FIG. 6, it may be seen that as the concentration of cDNA fragments increases, the number of optical marker particles in the image increases. That is, it may be seen that when quantitative analysis of the target nucleic acid molecule according to Present Example 1 is performed, the concentration of the target nucleic acid molecule can be measured accurately.

In one example, when detecting the target nucleic acid molecule based on a retro-reflective signal according to Present Example 1, a limit of detection (LOD) was calculated to be 34 pM. This may indicate a significant improvement over a limit of detection (LOD) of 10 nM of a conventional molecular beacon-based bio-sensing scheme employing the fluorophore disclosed in a following cited article:

Cited article: Sensitivity and Specificity of Metal Surface-Immobilized "Molecular Beacon" Biosensors, J. Am. Chem. Soc., 2005, vol. 127, pp. 7932-7940

From the above results, it may be seen that the method in accordance with the present disclosure may allow the target nucleic acid molecule to be measured more accurately than the bio-sensing method using the conventional expensive optical equipment while the method in accordance with the present disclosure requires the use of minimal optical devices such as the non-spectral white light source and the digital camera.

Present Example 2

To determine whether the retro-reflection principle-based gene biosensing scheme as developed in accordance with the present disclosure is applicable to analysis of single nucleotide polymorphism (SNP) as a major application field of the molecular beacon, following two genes: 'target gene' and 'verification gene' were quantitatively analyzed in the same manner as in Present Example 1 using the same molecular beacon and optical marker as in Present Example 1.

(i) target nucleic acid molecule (target gene): 5'-CTATGAGTTAAAGCTTGCTGAAGGTTATGA (SEQ ID NO: 3)-3'

(ii) verification nucleic acid molecule (verification gene): 5'-CTATGCGTTAAAGCGTGCTGAAGATTATGA (SEQ ID NO: 1)-3'

The verification nucleic acid molecule refers to DNA having three base pairs differing from those of the target nucleic acid molecule.

Experimental Example 2

FIG. 7 is a graph showing a result of gene analysis according to Present Example 2. Table 1 is a result showing a ratio of a signal intensity for the verification nucleic acid molecule to a signal intensity for the target nucleic acid molecule based on the concentration calculated from FIG. 7.

TABLE 1

| | Concentration | | | | | |
|---|---|---|---|---|---|---|
| | 0.01 nM | 0.1 nM | 1 nM | 10 nM | 100 nM | Average |
| Intensity ratio | 24.0% | 20.0% | 43.6% | 48.4% | 53.4% | 37.9% |

Referring to FIG. 6 and Table 1, it may be seen that although only three base pairs differ between the 'target gene' and 'verification gene', the intensity of the signal for the verification nucleic acid molecule is significantly reduced compared to the intensity for the signal of the target nucleic acid molecule. Specifically, the retro-reflective signal for the verification nucleic acid molecule was only about 38% of the retro-reflective signal for the target nucleic acid molecule.

From these results, it may be seen that the optical gene biosensor according to the present disclosure may be used in the field of gene mutation screening.

Although the present disclosure has been described with reference to the preferred embodiments of the present disclosure, those skilled in the art will appreciate that the present disclosure may be modified in various ways without departing from the spirit and scope of the present disclosure set forth in the claims below.

What is claimed is:

1. An optical gene biosensor comprising:
    a substrate;
    a molecular beacon anchored to the substrate, wherein the molecular beacon includes an oligonucleotide and a first compound, wherein the oligonucleotide is capable of specifically binding to a target nucleic acid, and wherein the first compound is bound to a first terminal of the oligonucleotide;
    an optical marker configured to retro-reflect irradiated light;
    a light source for irradiating the optical marker with light; and
    a light-receiver for receiving light retro-reflected from the optical marker;
    wherein the optical marker includes:
        a second compound specifically binding to the first compound, wherein the second compound is coupled to a to-be-modified layer;
        a transparent core particle;
        a total-reflection inducing layer to cover a portion of a surface of the core particle, wherein the total-reflection inducing layer is made of a material having a refractive index lower than a refractive index of the core particle in a visible light wavelength range of 360 nm to 820 nm;
        the to-be-modified layer formed on the total-reflection inducing layer; and
        a magnetic layer made of magnetic material, wherein the magnetic layer is placed between the total-reflection inducing layer and the to-be-modified layer.

2. The optical gene biosensor of claim 1, wherein the oligonucleotide includes:
    a loop section having base sequences complementary to base sequences of the target nucleic acid molecule;
    a first stem section extending from a first terminal of the loop section and having a terminal coupled to the first compound; and
    a second stem section extending from a second terminal of the loop section opposite to the first terminal of the loop section and having base sequences complementary to base sequences of the first stem section, wherein the second stem section is bound to the substrate.

3. The optical gene biosensor of claim 2, wherein the loop section includes 20 to 40 base sequences, wherein each of the first and second stem sections includes 4 to 8 base sequences.

4. The optical gene biosensor of claim 2, wherein the molecular beacon further includes a first spacer compound connecting the first compound to the terminal of the first stem section, wherein the first spacer compound includes an alkyl chain having 4 to 10 carbons or mini-poly(ethylene glycol) having about 4 to 10 repeating units.

5. The optical gene biosensor of claim 2, wherein the second stem section is bound to the substrate by a functional group attached to a terminal of the second stem section and covalently bonding to the substrate.

6. The optical gene biosensor of claim 5, wherein the molecular beacon further includes a second spacer compound connecting the functional group to a terminal of the second stem section, wherein the second spacer compound includes an alkyl chain having 4 to 10 carbons or mini-poly (ethylene glycol) having about 4 to 10 repeating units.

7. The optical gene biosensor of claim 1, wherein the core particle is made of one selected from the group consisting of silica, glass, polystyrene, and polymethyl methacrylate having a refractive index of 1.4 or greater in the visible wavelength range.

8. The optical gene biosensor of claim 7, wherein the total-reflection inducing layer is made of at least one selected from the group consisting of aluminum (Al), copper (Cu), gold (Au), silver (Ag), and zinc (Zn).

9. The optical gene biosensor of claim 1, wherein the core particle has an average diameter of 600 nm or greater and 2 μm or smaller, wherein the total-reflection inducing layer covers 30% to 70% of the surface of the core particle.

10. The optical gene biosensor of claim 9, wherein the total-reflection inducing layer has a thickness of 10 to 100 nm.

11. The optical gene biosensor of claim 1, wherein the to-be-modified layer is made of at least one selected from the group consisting of platinum (Pt), gold (Au), and silver (Ag).

12. The optical gene biosensor of claim 1, wherein the light-source is placed above the optical marker, and irradiates the optical marker with mixed light of a plurality of wavelengths or light of a single wavelength,
    wherein the light-receiver is placed above the optical marker and is spaced apart from the light-source, wherein the light-receiver receives light generated from the light-source and then irradiated to the optical marker and then retro-reflected from the optical marker.

13. The optical gene biosensor of claim 12, wherein the light-source emits light in an inclined manner in a range of 0° exclusive to 45° inclusive with respect to a propagating direction of the retro-reflected light.

14. The optical gene biosensor of claim 12, wherein the light-receiver includes:
    an image generator for receiving the retro-reflected light and for imaging the light into an image signal; and
    an image analyzer for analyzing the image signal generated from the image generator.

15. The optical gene biosensor of claim 14, wherein the image analyzer counts a number of the optical markers based on the image signal and analyzes a concentration of the target nucleic acid molecule based on the number.

16. The optical gene biosensor of claim 14, wherein the image analyzer measures an amount of light retro-reflected from the optical marker based on the image signal, and analyzes a concentration of the target nucleic acid molecule based on the amount.

17. The optical gene biosensor of claim 1, wherein the first compound includes dinitrophenyl (DNP) and the second compound includes an anti-DNP antibody compound specifically binding to the DNP.

* * * * *

SEQUENCE LISTING

```
<160> NUMBER OF SEQ ID NOS: 3

<210> SEQ ID NO 1
<211> LENGTH: 29
<212> TYPE: DNA
<213> ORGANISM: Artificial Sequence
<220> FEATURE:
<223> OTHER INFORMATION: Synthetic construct

<400> SEQUENCE: 1
ctatgagtta aagcttgctg aaggttatg                                29

<210> SEQ ID NO 2
<211> LENGTH: 42
<212> TYPE: DNA
<213> ORGANISM: Artificial Sequence
<220> FEATURE:
<223> OTHER INFORMATION: Synthetic construct

<400> SEQUENCE: 2
gtgagctcat aaccttcagc aagctttaac tcataggctc ac                 42

<210> SEQ ID NO 3
<211> LENGTH: 30
<212> TYPE: DNA
<213> ORGANISM: Artificial sequence
<220> FEATURE:
<223> OTHER INFORMATION: Syntehtic construct

<400> SEQUENCE: 3
ctatgagtta aagcttgctg aaggttatga                               30
```